(12) United States Patent
Sakuta

(10) Patent No.: US 6,585,985 B2
(45) Date of Patent: Jul. 1, 2003

(54) LIPSTICK COMPOSITION CONTAINING HYDROPHILIC CROSSLINKED SILICONE

(75) Inventor: Koji Sakuta, Gunma-ken (JP)

(73) Assignee: Shin-Etsu Chemical Co., Ltd., Tokyo (JP)

(*) Notice: Subject to any disclaimer, the term of this patent is extended or adjusted under 35 U.S.C. 154(b) by 0 days.

(21) Appl. No.: 09/731,743

(22) Filed: Dec. 8, 2000

(65) Prior Publication Data

US 2001/0010823 A1 Aug. 2, 2001

(30) Foreign Application Priority Data

Dec. 8, 1999 (JP) .......................................... 11-348327

(51) Int. Cl.$^7$ ............................. A61K 6/00; A61K 7/04; A01N 25/00
(52) U.S. Cl. ........................... 424/401; 424/61; 424/64; 514/844; 514/845
(58) Field of Search ................... 424/401, 61; 514/844, 514/845

(56) References Cited

U.S. PATENT DOCUMENTS 5,266,321 A * 11/1993 Shukuzaki et al. ......... 424/401
6,177,091 B1 * 1/2001 Bara et al. .................. 424/401

* cited by examiner

*Primary Examiner*—Jose G. Dees
(74) *Attorney, Agent, or Firm*—Millen, White, Zelano & Branigan, P.C.

(57) ABSTRACT

Disclosed is a lipstick composition for molding into a lipstick capable of exhibiting excellent cosmetic finishing effect with remarkable sustainability and comfortable feeling of use. The most characteristic ingredient of the composition is a crosslinked hydrophilic organopolysiloxane insoluble in organic solvents obtained by the hydrosilation reaction between an organohydrogenpolysiloxane and an alkenyl-terminated polyoxyalkylene compound, which is combined with a liquid oily compound, solid or semisolid oily or waxy compound and pigments in specified weight proportions.

16 Claims, No Drawings

LIPSTICK COMPOSITION CONTAINING HYDROPHILIC CROSSLINKED SILICONE

BACKGROUND OF THE INVENTION

The present invention relates to a novel lipstick composition or, more particularly, to a lipstick composition capable of imparting the users thereof with a comfortable feeling of use and sustainedly exhibiting excellent effects of cosmetic finishing.

One of the serious defects in conventional lipsticks in general as applied to the lips is the poor sustainability of the cosmetic finishing therewith sometimes to cause contamination of clothes or blurry spreading of the lipstick color. Various proposals and attempts have been made heretofore in order to provide a solution for this problem. For example, a proposal is made for the formulation of a lipstick composition by compounding the composition with a vaporizable oil agent so that the oil agent in the coating layer of the lipstick on the lips is lost by evaporation leaving the coloring materials and the waxy ingredients alone on the surface of the lipstick-coating layer resulting in an improvement of the sustainability of the lipstick finishing effect. According to another proposal, the vaporizable oil agent is admixed with a film-forming ingredient such as a polymeric resin to form a polymeric film on the lip surface after evaporation of the oil agent from the lipstick coating layer contributing to the improvement of the sustainability of the cosmetic finishing with the lipstick.

In particular, proposals are made in Japanese Patent Kokai 1-168067, 7-267826, 8-225432, 9-48709, 9-48710, 9-71510, 9-143033, 9-143034, 10-36223 and 10-167930, according to which the lipstick composition is admixed with a silicone resin as a type of the above mentioned film-forming resinous ingredient. The silicone resins disclosed there, however, are each strongly water-repellent and solid at room temperature to exhibit strong adhesion to the lip surface and the lipstick compositions formulated therewith are unsatisfactory in respect of the warm-keeping behavior.

On the other hand, Japanese Patent Kokai 7-330547 discloses a method for improving the sustainability of the lipstick finishing by compounding the lipstick composition with a polyoxyalkylene-modified organopolysiloxane having hydrophilicity. This hydrophilic modified organopolysiloxane absorbs moisture from the lip surface to be imparted with an increased viscosity by means of which the sustainability of the lipstick finishing can be improved. The adhesion of this lipstick composition to the lip surface, however, is not high enough because the modified silicone is liquid at the human body temperature.

SUMMARY OF THE INVENTION

The present invention accordingly has an object, in view of the above described problems and disadvantages in the conventional lipstick compositions formulated with a film-forming resinous ingredient, to provide an improved lipstick composition used in the preparation of a lipstick which never imparts the user with a disordered feeling of use but gives a comfortable feeling and is capable of giving an excellently aesthetic cosmetic finishing effect with sustainability.

Thus, the lipstick composition provided by the present invention is a uniform blend which comprises:

(a) from 0.1 to 30% by weight of a crosslinked organopolysiloxane compound having at least one hydrophilic organic group in a molecule, which is insoluble in an organic solvent;

(b) from 10 to 90% by weight of an oily compound selected from the group consisting of liquid hydrocarbon compounds, esters, higher fatty acids, higher alcohols and silicone oils;

(c) from 5 to 50% by weight of an oil or fat which is solid or semisolid having a melting point of 25° C. or higher; and (d) from 1 to 50% by weight of a pigment, the balance to 100%, if any, being constituted of substances permissible as an ingredient in a cosmetic preparation.

In particular, the hydrophilic crosslinked organopolysiloxane as the component (a) is a reaction product between an organohydrogenpolysiloxane represented by the average unit formula

$$R_a H_b SiO_{(4-a-b)/2}, \quad (I)$$

in which R is an optionally halogenated monovalent hydrocarbon group selected from the group consisting of alkyl groups having 1 to 8 carbon atoms, allyl group, aryl groups and aralkyl groups, the subscript a is a positive number in the range from 1.0 to 2.5 and the subscript b is a positive number in the range from 0.001 to 1.0 with the proviso that a+b is a positive number in the range from 1.5 to 2.8, and an alkenyl-terminated polyoxyalkylene compound represented by the general formula

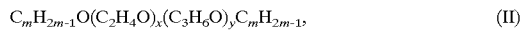

$$C_m H_{2m-1} O(C_2 H_4 O)_x (C_3 H_6 O)_y C_m H_{2m-1}, \quad (II)$$

in which the subscript x is a positive integer in the range from 2 to 200, the subscript y is 0 or a positive integer not exceeding 200 with the proviso that x+y is a positive integer in the range from 3 to 200 and the subscript m is a positive integer in the range from 2 to 6.

It is preferable that from 5 to 30% by moles of the groups denoted by R in the average unit formula (1) are optionally halogenated monovalent hydrocarbon groups having 6 to 30 carbon atoms, the balance to 100% being methyl groups.

DETAILED DESCRIPTION OF THE PREFERRED EMBODIMENTS

The above described unique formulation of the inventive lipstick composition has been established on the base of the unexpected findings of the inventors that, when a lipstick composition is compounded with a hydrophilic crosslinked organopolysiloxane compound, this organopolysiloxane compound in the coating layer on the lip surface absorbs moisture from the lip surface to be imparted with an increased viscosity and to exhibit a gel-like consistency and rubbery elasticity so that the layer of the lipstick composition adhesively coating the lip surface can smoothly follow the movement of the lips and the sustainability of the lipstick finishing can be greatly improved without adversely affecting the desirable properties obtained by the formulation with a hydrophilic organopolysiloxane compound.

In the hydrophilic crosslinked organopolysiloxane compound as the component (a) of the inventive lipstick composition, the hydrophilic organic group can be selected from a wide variety of known hydrophilic groups including polyoxyethylene groups, poly(oxyethyleneoxypropylene) copolymeric groups, polyvinylpyrrolidone groups, acrylic acid group, methacrylic acid group, phosphoric acid groups, polyoxyethylene phosphate ester groups and quaternary ammonium-substituted alkyl groups, though not particularly limited thereto.

While the hydrophilic crosslinked organopolysiloxane compound as the component (a) must be insoluble in or not freely miscible with an organic solvent, the organic solvent used in this insolubility test is exemplified by aliphatic hydrocarbon solvents having a straighty linear or branched molecular structure such as pentane, hexane, decane, hexadecane and octadecane, aromatic hydrocarbon solvents such as benzene, toluene and xylene, alcoholic solvents such as methanol, ethanol, propanol, butanol, haxanol and decanol, halogenated hydrocarbon solvents such as chloroform and carbon tetrachloride and ketone solvents such as acetone and methyl ethyl ketone.

The hydrophilic crosslinked organopolysiloxane can be prepared by several different methods, each of which is known in the art of silicone chemistry, including:

(1) the hydrosilation addition reaction between an organohydrogenpolysiloxane and a polyoxyalkylene compound terminated at each molecular chain end with an aliphatically unsaturated group;

(2) the radical copolymerization reaction of an organopolysiloxane having a radical-polymerizable group and a hydrophilic polymer having a radical-reactive group;

(3) the hydrosilation addition reaction between an organohydrogenpolysiloxane and a polyoxyalkylene diacryloyl ester compound;

(4) the addition reaction between an amino-modified organopolysiloxane and a polyoxyalkylene diglycidyl ether;

(5) the condensation reaction between a carboxylic acid-modified organopolysiloxane and a polyoxyalkyleneglycol; and (6) the hydrosilation addition reaction between a polyoxyalkylene-modified organohydrogenpolysiloxane and a vinyl group-containing organopolysiloxane or an organic compound having at least two aliphatically unsaturated groups in a molecule.

A preferable method, inter alia, is the method in which an organohydrogenpolysiloxane represented by the average unit formula

$$R_aH_bSiO_{(4-a-b)/2}, \quad (I)$$

in which R is an optionally halogenated monovalent hydrocarbon group selected from the group consisting of alkyl groups having 1 to 8 carbon atoms, allyl group, aryl groups and aralkyl groups, the subscript a is a positive number in the range from 1.0 to 2.5 and the subscript b is a positive number in the range from 0.001 to 1.0 with the proviso that a+b is a positive number in the range from 1.5 to 2.8, and having at least three silicon-bonded hydrogen atoms in a molecule is reacted with an alkenyl-terminated polyoxyalkylene compound represented by the general formula

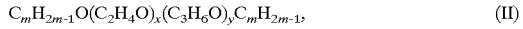

$$C_mH_{2m-1}O(C_2H_4O)_x(C_3H_6O)_yC_mH_{2m-1}, \quad (II)$$

in which the subscript x is a positive integer in the range from 2 to 200, the subscript y is 0 or a positive integer not exceeding 200 with the proviso that x+y is a positive integer in the range from 3 to 200 and the subscript m is a positive integer in the range from 2 to 6.

In the organohydrogenpolysiloxane represented by the average unit formula (I), it is preferable that from 5 to 30% by moles of the groups denoted by R are hydrocarbon groups having 6 to 30 carbon atoms, the balance to 100% being methyl groups.

In the component (a) formulated in the inventive lipstick composition, the groups denoted by R in the average unit formula (I) are each, independently from the others, a monovalent hydrocarbon group having 1 to 30 carbon atoms selected from the group consisting of alkyl groups, allyl group, aryl groups and aralkyl groups as well as halogenated hydrocarbon groups derived from these hydrocarbon groups. Particular examples of the monovalent hydrocarbon groups include alkyl groups such as methyl, ethyl, propyl, butyl, pentyl, hexyl, heptyl, octyl, nonyl, decyl, dodecyl, hexadecyl, octadecyl, eicosyl, octacosyl and triacontyl groups, cycloalkyl groups such as cyclopentyl group, aryl groups such as phenyl and tolyl groups, aralkyl groups such as benzyl and phenethyl groups and halogenated hydrocarbon groups such as trifluoropropyl and chlorophenyl groups.

The subscript a in the average unit formula (I) is a positive number in the range from 1.0 to 2.5 or, preferably, from 1.5 to 2.3. When the value of the subscript a is too small, the density of crosslinks in the crosslinked organopolysiloxane prepared from the organohydrogenpolysiloxane as the component (a) would be unduly high so that the coating layer of the lipstick composition on the lip surface cannot follow the movement of the lips to cause a disordered feeling to the lips. When the value of a is too large, on the other hand, the density of crosslinks in the crosslinked organopolysiloxane as the component (a) is unduly low not to be insoluble in organic solvents so that the sustainability of the cosmetic finish with the lipstick is decreased.

The value of the subscript b in the average unit formula (I) is a positive number in the range from 0.01 to 1.0 or, preferably, from 0.05 to 0.8. When the value of b is too small, the crosslinking density of the crosslinked organopolysiloxane as the component (a) cannot be high enough not to be insoluble in organic solvents resulting in a decrease in the sustainability of the cosmetic finish with the lipstick. When the value of b is too large, on the other hand, the crosslinking density of the crosslinked organopolysiloxane as the component (a) is unduly increased so that the coating layer of the lipstick composition on the lip surface cannot smoothly follow the movement of the lips to impart the user with a disordered feeling.

It is important that the values of the subscripts a and b are selected in such a way as to satisfy the proviso that a+b is in the range from 1.5 to 2.8 or, preferably, from 1.7 to 2.5. An unduly small value of a+b means an excessively high crosslinking density in the crosslinked organopolysiloxane as the component (a) so that the coating layer of the lipstick composition on the lip surface cannot smoothly follow the movement of the lips to impart the user with a disordered feeling. When the value of a+b is too large, on the other hand, the crosslinked organopolysiloxane has an unduly decreased crosslinking density not to be insoluble in organic solvents.

In the general formula (II) representing the polyoxyalkylene compound to be reacted with the organohydrogenpolysiloxane to form the crosslinked organopolysiloxane as the component (a), the subscript x is a positive integer in the range from 2 to 200. When the subscript x is 0 or 1, the crosslinked organopolysiloxane cannot be imparted with high hydrophilicity. When the total of the values of the subscripts x and y, i.e. x+y, is larger than 200, the degree of polymerization of the hydrophilic groups is unduly high so that an undue increase is caused in the viscosity of the crosslinked organopolysiloxane, which cannot be fully miscible with the oily ingredients. When the subscript m is larger than 6, the degree of polymerization of the alkenyl group expressed by the formula —$C_mH_{2m-1}$ is too large so that the polyoxyalkylene compound cannot be fully hydrophilic.

In the component (a) formulated in the inventive lipstick composition, the organohydrogenpolysiloxane is constituted from several types of siloxane units including those expressed by the unit formulas including $RSiO_{1.5}$, $R_2SiO$, $R_3SiO_{0.5}$, $RHSiO$, $R_2HSiO_{0.5}$, $HSiO_{1.5}$ and $SiO_2$, in which R has the same meaning as defined before. The molecular structure of this organohydrogenpolysiloxane can be straightly linear, branched or cyclic but a straightly linear molecular structure is preferable.

In the preparation of the inventive lipstick composition, the above described hydrophilic crosslinked organopolysiloxane compound as the component (a) can be compounded as such with the other essential ingredients and optional ingredients. It is, however, more convenient and more efficient that 100 parts by weight of the component (a) are blended in advance with 10 to 1000 parts by weight of an oily liquid substance as the component (b) to give a pasty premix and this premix is compounded with the other ingredients.

The crosslinked organopolysiloxane as the component (a) is prepared by the hydrosilation addition reaction between the organohydrogenpolysiloxane represented by the average unit formula (I) and the polyoxyalkylene compound represented by the general formula (II). The reaction is performed at room temperature or at an elevated temperature of 50 to 150° C. in the presence of a catalyst which is a platinum compound such as chloroplatinic acid, alcohol-modified chloroplatinic acid, complex of chloroplatinic acid and a vinyl siloxane and the like as well as rhodium compounds similar thereto.

The above mentioned addition reaction can be conducted in a solution of the reactants and catalyst dissolved in an organic solvent which can be selected from the group consisting of aliphatic alcohols such as methanol, ethanol, 2-propanol and butanol, aromatic hydrocarbon solvents such as benzene, toluene and xylene, aliphatic or alicyclic hydrocarbon solvents such as n-pentane, n-hexane and cyclohexane, and halogenated hydrocarbon solvents including chlorinated hydrocarbon compounds such as dichloromethane, chloroform, carbon tetrachloride, trichloroethane, trichloroethylene and fluorinated hydrocarbon compounds, of which ethanol and 2-propanol are preferred in consideration of the intended application of the reaction product as an ingredient in a cosmetic preparation.

The component (b) in the inventive lipstick composition is an oily liquid at room temperature which can be selected from the group consisting of liquid hydrocarbon compounds such as liquid paraffin, squalane and pristane, fatty acid esters having 6 to 50 carbon atoms in a molecule such as cetyl isooctanoate, octyldodecyl myristate, isopropyl palmitate, isocetyl stearate and octyldodecyl oleate, triglyceride oils such as glycerin trioctanoate and glycerin triisostearate, higher fatty acids having 6 to 50 carbon atoms in a molecule such as isostearic acid, oleic acid, hexanoic acid and heptanoic acid, aliphatic higher alcohols having 6 to 50 carbon atoms in a molecule, such as isostearyl alcohol and oleyl alcohol, cyclic or straightly linear organopolysiloxanes such as octamethyl cyclotetrasiloxane, decamethyl cyclopentasiloxane, dimethylpolysiloxane oils and methylphenylpolysiloxane oils. These oily compounds can be used either singly or as a combination of two kinds or more, if compatible, as the component (b). These oily compounds should have a viscosity in the range from 1.0 to 1000 $mm^2$/second at 25° C.

Preferable among the above named oily compounds as the component (b) are hydrocarbon compounds such as liquid paraffins and squalane and branched fatty acid esters. The branched fatty acid ester is preferably a branched monoester of a monohydric alcohol having at least 3 carbon atoms in a molecule and an aliphatic monocarboxylic acid having at least 3 carbon atoms in a molecule, a branched diester of a monohydric alcohol having at least 3 carbon atoms in a molecule and an aliphatic dicarboxylic acid having at least 3 carbon atoms in a molecule, a branched diester of a dihydric alcohol having at least 3 carbon atoms in a molecule and an aliphatic monocarboxylic acid having at least 3 carbon atoms in a molecule, a branched triester of a monohydric alcohol having at least 3 carbon atoms in a molecule and an aliphatic tricarboxylic acid having at least 3 carbon atoms in a molecule and a branched triester of a trihydric alcohol having at least 3 carbon atoms in a molecule and an aliphatic monocarboxylic acid having at least 3 carbon atoms in a molecule.

Particular examples of such a branched fatty acid ester compound include monoesters such as isotridecyl isononanoate, isostearyl myristate, isostearyl isopalmitate and isopropyl isostearate, diesters such as neopentylglycol dicaprylate and triesters such as trimethylolpropane triisostearate.

Examples of the oil or fat which is solid or semisolid at room temperature having a melting point in the range from 25 to 300° C. as the component (c) of the inventive lipstick composition include Japan wax, hardened beef tallow, carnauba wax, candelilla wax, rice wax, beeswax, microcrystalline wax, paraffin wax, polyethylene wax, hardened jojoba oil, lanolin and petrolatum.

The pigment as the component (d) in the inventive lipstick composition can be selected from those conventionally formulated in cosmetic and toiletry preparations. Examples of suitable pigments include body pigments such as talc, cerisite, mica, kaolin, silica, nylon powders, polyethylene powders and cellulose powders, inorganic coloring pigments such as carbon black, titanium dioxide, iron oxides, zinc oxide, ultramarine, Prussian blue, organic tar-based coloring pigments and lakes and composite pigments such as titanium mica and iron oxide-coated micas. If necessary, these pigments can be surface-treated with a known surface treatment agent such as silicones, higher fatty acids, higher alcohols, fatty acid esters, metal soaps, amino acids and alkyl phosphates.

It is of course optional according to need that the inventive lipstick composition is compounded, besides the above described essential ingredients, with a variety of known additives including oily materials other than those mentioned above, surface active agents, medicinally effective compounds, antiseptic agents, antioxidants, moisturizing agents, intercellular lipids, e.g., ceramide, ultraviolet absorbers and perfumes each in a limited amount.

Care should be taken in the preparation of the inventive lipstick composition that the amount of water introduced into the composition should be as small as possible because water contained in the lipstick composition has an adverse influence on the sustainability of the cosmetic finish therewith. Accordingly, the above described essential and optional ingredients each should be dry and anhydrous or free of moisture.

The lipstick composition of the invention can be prepared according to a known procedure by uniformly blending or kneading together the above described essential and optional ingredients, if necessary, under heating.

In the following, the lipstick composition of the present invention is described in more detail by way of Examples, which, however, never limit the scope of the invention in any way, as preceded by Synthetic Examples for the preparation of the hydrophilic crosslinked organopolysiloxanes to be used as the component (a).

SYNTHETIC EXAMPLE 1

Into a reaction vessel were taken 100 g of an organohydrogenpolysiloxane expressed by the structural formula

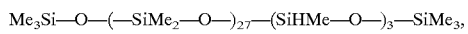
$$Me_3Si—O—(—SiMe_2—O—)_{27}—(SiHMe—O—)_3—SiMe_3,$$

In which Me is a methyl group, 103.0 g of ethanol, 23.6 g of an allyl-terminated polyoxyethylene expressed by the average formula

$$CH_2=CHCH_2—O—(C_2H_4O)_{10}—CH_2CH=CH_2,$$

and 0.3 g of a 3% by weight ethanol solution of chloroplatinic acid to form a reaction mixture which was agitated at a temperature of 70 to 80° C. for 2 hours followed by removal of the ethanol by distillation under reduced pressure to give a crosslinked organopolysiloxane exhibiting elastic resilience.

In the next place, a 100 g portion of this crosslinked organopolysiloxane was compounded with 300 g of a dimethylpolysiloxane oil having a viscosity of 6 mm²/second at 25° C. on a three-roller mill to give a uniform blend having pasty consistency, which is referred to as the silicone composition 1 hereinafter.

SYNTHETIC EXAMPLE 2

Into a reaction vessel were taken 323 g of an organohydrogenpolysiloxane expressed by the structural formula

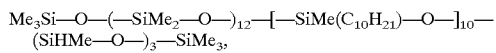
$$Me_3Si—O—(—SiMe_2—O—)_{12}—[—SiMe(C_{10}H_{21})—O—]_{10}—(SiHMe—O—)_3—SiMe_3,$$

In which Me is a methyl group, 120.0 g of ethanol, 98.0 g of an allyl-terminated polyoxyalkylene expressed by the average formula

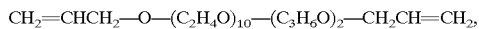
$$CH_2=CHCH_2—O—(C_2H_4O)_{10}—(C_3H_6O)_2—CH_2CH=CH_2,$$

and 0.3 g of a 3% by weight ethanol solution of chloroplatinic acid to form a reaction mixture which was agitated at a temperature of 70 to 80° C. for 2 hours followed by removal of the ethanol by distillation under reduced pressure to give a crosslinked organopolysiloxane exhibiting elastic resilience.

In the next place, a 100 g portion of this crosslinked organopolysiloxane was compounded with 400 g of cetyl isooctanoate on a three-roller mill to give a uniform blend having pasty consistency, which is referred to as the silicone composition 2 hereinafter.

SYNTHETIC EXAMPLE 3

Into a reaction vessel were taken 446.4 g of an organohydrogenpolysiloxane expressed by the structural formula

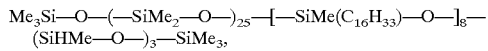
$$Me_3Si—O—(—SiMe_2—O—)_{25}—[—SiMe(C_{16}H_{33})—O—]_8—(SiHMe—O—)_3—SiMe_3,$$

In which Me is a methyl group, 200.0 g of ethanol, 88.0 g of an allyl-terminated polyoxyethylene expressed by the average formula

$$CH_2=CHCH_2—O—(C_2H_4O)_{20}—CH_2CH=CH_2,$$

and 0.3 g of a 3% by weight ethanol solution of chloroplatinic acid to form a reaction mixture which was agitated at a temperature of 70 to 80° C. for 2 hours followed by removal of the ethanol by distillation under reduced pressure to give a crosslinked organopolysiloxane exhibiting elastic resilience.

In the next place, a 100 g portion of this crosslinked organopolysiloxane was compounded with 400 g of squalane on a three-roller mill to give a uniform blend having pasty consistency, which is referred to as the silicone composition 3 hereinafter.

EXAMPLE 1

Eleven ingredients (1) to (11) were taken in the proportion shown below and the blend was uniformly melted at 80° C. The melt was cast into a mold for shaping and solidified therein to give a lipstick of the composition.

| Ingredient | % by wt. |
| --- | --- |
| (1) Silicone composition 1 | 7.0 |
| (2) Candelilla wax | 5.0 |
| (3) Polyethylene wax | 12.0 |
| (4) Microcrystalline wax | 4.0 |
| (5) Polybutene | 5.0 |
| (6) Isocetyl octanoate | 20.0 |
| (7) Isodecyl isononanoate | 7.0 |
| (8) Glyceryl isostearate | 33.0 |
| (9) Sucrose fatty acid ester | 3.0 |
| (10) Titanium dioxide | 2.0 |
| (11) Red #201 | 2.0 |
| Total | 100.0 |

The thus prepared lipsticks were subjected to an organoleptic evaluation test by 10 expert female testing members, each of whom was requested to express her evaluation of the lipstick as "good" or "poor" for each of the six testing items including:

(i) spreadability over the lip surface;

(ii) adhesion to the lip surface;

(iii) preference of cosmetic finish;

(iv) color falling over time;

(v) contamination by color transfer over time; and (vi) marginal blur over time.

The results of the organoleptic evaluation test reported by the 10 members were recorded in four ratings of A, B, C and D for each testing item according to the criteria that:

A was given when 8 or more of the 10 testing members expressed their evaluation of "good";

B was give when 6 or 7 of the 10 testing members expressed their evaluation of "good";

C was given when 4 or 5 of the 10 testing members expressed their evaluation of "good"; and D was give when 3 or less of the 10 testing members expressed their evaluation of "good".

The results are summarized in Table 1 below for each of the testing items.

EXAMPLE 2

The procedure for the preparation and evaluation of lipsticks was substantially the same as in Example 1 except that the lipstick composition was prepared according to the following formulation with 12 ingredients.

| Ingredient | % by wt. |
| --- | --- |
| (1) Silicone composition 1 | 10.0 |
| (2) Ceresin wax | 10.0 |

-continued

| Ingredient | % by wt. |
|---|---|
| (3) Paraffin wax | 8.0 |
| (4) Candelilla wax | 2.0 |
| (5) Liquid paraffin | 22.0 |
| (6) Liquid lanolin | 10.0 |
| (7) Isodecyl isononanoate | 25.0 |
| (8) Decamethyl cyclopentasiloxane | 5.0 |
| (9) Titanium dioxide | 2.0 |
| (10) Red #202 | 2.0 |
| (11) Red #201 | 1.0 |
| (12) Yellow #4 Al lake | 3.0 |
| Total | 100.0 |

The results of the organoleptic evaluation test are shown in Table 1.

EXAMPLE 3

The procedure for the preparation and evaluation of lipsticks was substantially the same as in Example 1 except that the lipstick composition was prepared according to the following formulation with 11 ingredients.

| Ingredient | % by wt. |
|---|---|
| (1) Silicone composition 2 | 7.0 |
| (2) Candelilla wax | 5.0 |
| (3) Polyethylene wax | 12.0 |
| (4) Microcrystalline wax | 4.0 |
| (5) Polybutene | 5.0 |
| (6) Isocetyl octanoate | 20.0 |
| (7) Isodecyl isononanoate | 7.0 |
| (8) Glyceryl isostearte | 33.0 |
| (9) Sucrose fatty acid ester | 3.0 |
| (10) Titanium dioxide | 2.0 |
| (11) Red #201 | 2.0 |
| Total | 100.0 |

The results of the organoleptic evaluation test are shown in Table 1.

EXAMPLE 4

The procedure for the preparation and evaluation of lipsticks was substantially the same as in Example 1 except that the lipstick composition was prepared according to the following formulation with 12 ingredients.

| Ingredient | % by wt. |
|---|---|
| (1) Silicone composition 3 | 10.0 |
| (2) Ceresin wax | 10.0 |
| (3) Paraffin wax | 8.0 |
| (4) Candelilla wax | 2.0 |
| (5) Liquid paraffin | 22.0 |
| (6) Liquid lanolin | 10.0 |
| (7) Isodecyl isononanoate | 25.0 |
| (8) Decamethyl cyclopentasiloxane | 5.0 |
| (9) Titanium dioxide | 2.0 |
| (10) Red #201 | 2.0 |
| (11) Red #202 | 1.0 |
| (12) Yellow #4 Al lake | 3.0 |
| Total | 100.0 |

The results of the organoleptic evaluation test are shown in Table 1.

EXAMPLE 5

The procedure for the preparation and evaluation of lipsticks was substantially the same as in Example 1 except that the lipstick composition was prepared according to the following formulation with 10 ingredients.

| Ingredient | % by wt. |
|---|---|
| (1) Silicone composition 3 | 8.0 |
| (2) Polyethylene wax | 12.0 |
| (3) Microcrystalline wax | 4.0 |
| (4) Acrylic/silicone copolymer *) | 12.0 |
| (5) Polybutene | 5.0 |
| (6) Isocetyl octanoate | 20.0 |
| (7) Glyceryl isostearate | 32.0 |
| (8) Sucrose fatty acid ester | 3.0 |
| (9) Titanium dioxide | 2.0 |
| (10) Red #201 | 2.0 |
| Total | 100.0 |

*) 50:40:10 by weight copolymer of dimethylpolysiloxane (degree of polymerization 30) monomethacrylate, stearyl methacrylate and methyl methacrylate The results of the organoleptic evaluation test are shown in Table 1.

COMPARATIVE EXAMPLE 1

The procedure for the preparation and evaluation of lipsticks was substantially the same as in Example 1 except that the lipstick composition was prepared according to the following formulation with 12 ingredients.

| Ingredient | % by wt. |
|---|---|
| (1) Ceresin wax | 10.0 |
| (2) Paraffin wax | 8.0 |
| (3) Candelilla wax | 2.0 |
| (4) POE-modified silicone **) | 10.0 |
| (5) Polybutene | 12.0 |
| (6) Liquid paraffin | 20.0 |
| (7) Liquid lanolin | 10.0 |
| (8) Isocetyl octanoate | 20.0 |
| (9) Titanium dioxide | 2.0 |
| (10) Red #201 | 2.0 |
| (11) Red #202 | 1.0 |
| (12) Yellow #4 Al lake | 3.0 |
| Total | 100.0 |

**) molecular weight 4000, content of polyoxyethylene 23% by weight

The results of the organoleptic evaluation test are shown in Table 1.

COMPARATIVE EXAMPLE 2

The procedure for the preparation and evaluation of lipsticks was substantially the same as in Example 1 except that the lipstick composition was prepared according to the following formulation with 12 ingredients.

| Ingredient | % by wt. |
|---|---|
| (1) Ceresin wax | 10.0 |
| (2) Paraffin wax | 8.0 |
| (3) Candelilla wax | 2.0 |

-continued

| Ingredient | % by wt. |
|---|---|
| (4) Trimethylsiloxy silicate | 10.0 |
| (5) Polybutene | 12.0 |
| (6) Liquid lanolin | 10.0 |
| (7) Squalane | 20.0 |
| (8) Isodecyl isononanoate | 20.0 |
| (9) Titanium dioxide | 2.0 |
| (10) Red #201 | 2.0 |
| (11) Red #202 | 1.0 |
| (12) Yellow #4 Al lake | 3.0 |
| Total | 100.0 |

The results of the organoleptic evaluation test are shown in Table 1.

COMPARATIVE EXAMPLE 3

The procedure for the preparation and evaluation of lipsticks was substantially the same as in Example 1 except that the lipstick composition was prepared according to the following formulation with 12 ingredients.

| Ingredient | % by wt. |
|---|---|
| (1) Silicone composition 3 | 10.0 |
| (2) Candelilla wax | 5.0 |
| (3) Polyethylene wax | 12.0 |
| (4) Microcrystalline wax | 4.0 |
| (5) Purified water | 3.0 |
| (6) Polybutene | 5.0 |
| (7) Isocetyl octanoate | 20.0 |
| (8) Isodecyl isononanoate | 1.0 |
| (9) Glyceryl isostearate | 33.0 |
| (10) Sucrose fatty acid ester | 3.0 |
| (11) Titanium dioxide | 2.0 |
| (12) Red #201 | 2.0 |
| Total | 100.0 |

The results of the organoleptic evaluation test are shown in Table 1.

TABLE 1

| Testing item | Example | | | | | Comparative Example | | |
|---|---|---|---|---|---|---|---|---|
| | 1 | 2 | 3 | 4 | 5 | 1 | 2 | 3 |
| i | A | A | A | A | A | D | D | C |
| ii | B | B | B | B | A | D | C | B |
| iii | A | A | A | A | A | C | C | B |
| iv | B | B | A | A | A | B | B | D |
| v | B | B | A | A | A | C | B | D |
| vi | B | A | A | A | A | C | C | C |

What is claimed is:

1. A lipstick composition which comprises, as a uniform blend:
   (a) from 0.1 to 30% by weight of a crosslinked organopolysiloxane compound having at least one hydrophilic group in a molecule, and insoluble in an organic solvent;
   in which the crosslinked organopolysiloxane is a reaction product between
   (i) an organohydrogenpolysiloxane represented by the average unit formula (I)

$R_aH_bSiO_{(4-a-b)/2}$, in which R is an unsubstituted or halogen-substituted monovalent hydrocarbon group selected from the group consisting of alkyl groups having 1 to 8 carbon atoms, allyl group, aryl groups and aralkyl groups, the subscript a is a positive number in the range from 1.0 to 2.5 and the subscript b is a positive number in the range from 0.001 to 1.0 with the proviso that a+b is a positive number in the range from 1.5 to 2.8, and
   (ii) an alkylenyl-terminated polyoxyalkylene compound represented by the formula (II)

$C_mH_{2m-1}O(C_2H_4O)_x(C_3H_6O)_yC_mH_{2m-1}$, in which the subscript x is a positive integer in the range from 2 to 200, the subscript y is 0 or a positive integer not exceeding 200 with the proviso that x+y is a positive integer in the range from 3 to 200 and the subscript m is a positive integer in the range from 2 to 6,
   (b) from 10 to 90% by weight of an oily compound having a viscosity in the range from 1 to 1000 mm²/second at 25° C. selected from the group consisting of liquid hydrocarbon compounds, esters, higher fatty acids, higher alcohols and liquid silicone compounds;
   (c) from 5 to 50% by weight of an oil or fat which is solid or semisolid at room temperature; and
   (d) from 1 to 50% by weight of a pigment, the balance to 100%, if any, being additives permissible as an ingredient of a cosmetic preparation.

2. The lipstick composition as claimed in claim 1 in which the crosslinked organopolysiloxane as the component (a) is a reaction product between an organohydrogenpolysiloxane represented by the average unit formula $R_aH_bSiO_{(4-a-b)/2}$, In which R is an unsubstituted or halogen-substituted monovalent hydrocarbon group selected from the group consisting of alkyl groups having 1 to 8 carbon atoms, allyl group, aryl groups and aralkyl groups, the subscript a is a positive number in the range from 1.0 to 2.5 and the subscript b is a positive number in the range from 0.001 to 1.0 with the proviso that a+b is a positive number in the range from 1.5 to 2.8, and an alkylenyl-terminated polyoxyalkylene compound represented by the general formula $C_mH_{2m-1}O(C_2H_4O)_x(C_3H_6O)_yC_mH_{2m-1}$, In which the subscript x is a positive integer in the range from 2 to 200, the subscript y is 0 or a positive integer not exceeding 200 with the proviso that x+y is a positive integer in the range from 3 to 200 and the subscript m is a positive integer in the range from 2 to 6.

3. The lipstick composition as claimed in claim 1 in which from 5 to 30% by moles of the groups denoted by R in the organohydrogen-polysiloxane are each a monovalent unsubstituted hydrocarbon group or a halogenated hydrocarbon group having 6 to 30 carbon atoms, the balance to 100% by moles being methyl groups.

4. The lipstick composition as claimed in claim 1 in which the organic solvent in which the crosslinked organopolysiloxane as the component (a) is insoluble is selected from the group consisting of aliphatic hydrocarbon compounds, aromatic hydrocarbon compounds, alcohols and aliphatic halogenated hydrocarbon compounds.

5. The lipstick composition as claimed in claim 1 in which the sum of the subscripts a and b in the average unit formula representing the organohydrogenpolysiloxane is a positive number in the range from 1.7 to 2.5.

6. The lipstick composition as claimed in claim 1 in which the liquid hydrocarbon compound as the component (b) is selected from the group consisting of liquid paraffin, squalane and pristane.

7. The lipstick composition as claimed in claim 1 in which the ester as the component (b) is selected from the group consisting of cetyl isooctanoate, octyl dodecylte, isopropyl palmitate, isocetyl stearate, octyl dodecyl oleate, glyceryl trioctanoate and glyceryl triisostearate.

8. The lipstick composition as claimed in claim 1 in which the higher fatty acid as the component (b) is selected from the group consisting of isostearic acid, oleic acid, hexanoic acid and heptanoic acid.

9. The lipstick composition as claimed in claim 1 in which the higher alcohol as the component (b) is selected from the group consisting of isostearyl alcohol and oleyl alcohol.

10. The lipstick composition as claimed in claim 1 in which the liquid silicone compound as the component (b) is selected from the group consisting of octamethyl cyclotetrasiloxane, decamethyl cyclopentasiloxane, dimethylpolysiloxane oils and methylphenylpolysiloxane oils.

11. The lipstick composition as claimed in claim 1 in which the hydrophilic group in the component (a) is selected from the group consisting of polyoxyethylene groups, poly(oxyethylene-oxypropylene) copolymeric groups, polyvinylpyrrolidone groups, acrylic acid group, methacrylic acid group, phosphoric acid group, polyoxyethylene phosphoric acid ester groups and quaternary ammonium salt group-substituted alkyl groups.

12. The lipstick composition as claimed in claim 11 in which the hydrophilic group in the component (a) is selected from the group consisting of polyoxyethylene groups and poly(oxyethylene-oxypropylene) copolymeric groups.

13. A lipstick composition according to claim 1, wherein the value of the subscript b in the average unit formula (I) is a positive number in the range from 0.05 to 0.8.

14. A lipstick composition according to claim 1, in which component (b) is a branched fatty acid ester.

15. A lipstick composition according to claim 14, in which component (b) the branched fatty acid ester is a branched monoester of a monohydric alcohol having at least 3 carbon atoms in a molecule and an aliphatic monocarboxylic acid having at least 3 carbon atoms in a molecule, a branched diester of a monohydric alcohol having at least 3 carbon atoms in a molecule and an aliphatic dicarboxylic acid having at least 3 carbon atoms in a molecule, a branched diester of a dihydric alcohol having at least 3 carbon atoms in a molecule and an aliphatic monocarboxylic acid having at least 3 carbon atoms in a molecule, a branched triester of a monohydric alcohol having at least 3 carbon atoms in a molecule and an aliphatic tricarboxylic acid having at least 3 carbon atoms in a molecule, and a branched triester of a trihydric alcohol having at least 3 carbon atoms in a molecule and an aliphatic monocarboxylic acid having at least 3 carbon atoms in a molecule.

16. A lipstick composition according to claim 1, in which component (b) is isotridecyl isononanoate, isostearyl myristate, isostearyl isopalmitate, isopropyl isostearate, neopentylglycol dicaprylate and trimethylolpropane triisostearate.

* * * * *